United States Patent [19]

Pearson et al.

[11] Patent Number: 5,658,259
[45] Date of Patent: Aug. 19, 1997

[54] DENTAL CARTRIDGE ASSEMBLY AUTO-INJECTOR WITH PROTECTIVE NEEDLE COVER

[75] Inventors: William R. Pearson, Laurel, Md.; David Edward Spady, Centreville, Va.; Claudio Lopez, Darnstown, Md.; Hyung J. Lee, Cary, N.C.; John G. Wilmot, Germantown, Md.; N. Lawrence Dalling, Cross Junction, Va.

[73] Assignee: Meridian Medical Technologies, Inc., Columbia, Md.

[21] Appl. No.: 545,149

[22] Filed: Oct. 19, 1995

[51] Int. Cl.⁶ ............................................. A61M 5/00
[52] U.S. Cl. ..................... 604/232; 604/136; 604/208
[58] Field of Search ........................ 604/232, 218, 604/192, 263, 187, 136, 135, 134, 208

[56] References Cited

U.S. PATENT DOCUMENTS

| | | |
|---|---|---|
| 2,752,918 | 7/1956 | Uytenbogaart . |
| 2,887,108 | 5/1959 | Kendall . |
| 3,368,557 | 2/1968 | Hassing et al. . |
| 3,413,974 | 12/1968 | Cohen . |
| 3,678,931 | 7/1972 | Cohen . |
| 3,797,489 | 3/1974 | Sarnoff . |
| 3,825,003 | 7/1974 | Kruck . |
| 3,880,163 | 4/1975 | Ritterskamp . |
| 3,941,130 | 3/1976 | Tibbs . |
| 4,445,895 | 5/1984 | Margulies . |
| 4,664,654 | 5/1987 | Strauss . |
| 5,114,033 | 5/1992 | Golias et al. . |
| 5,114,406 | 5/1992 | Gabriel et al. . |
| 5,122,119 | 6/1992 | Lucas . |
| 5,176,643 | 1/1993 | Kramer et al. . |
| 5,226,895 | 7/1993 | Harris . |
| 5,226,896 | 7/1993 | Harris . |
| 5,383,865 | 1/1995 | Michel .................... 604/232 |
| 5,540,664 | 7/1996 | Wyrick .................... 604/136 |
| 5,582,598 | 12/1996 | Chanoch .................. 604/208 |

FOREIGN PATENT DOCUMENTS

| | | |
|---|---|---|
| 0 361 668 A1 | 4/1990 | European Pat. Off. . |
| 0 416 353 A1 | 3/1991 | European Pat. Off. . |
| WO89/12473 | 12/1989 | WIPO . |
| WO91/01153 | 2/1991 | WIPO . |

*Primary Examiner*—John D. Yasko
*Attorney, Agent, or Firm*—Cushman Darby & Cushman Intellectual Property Group of Pillsbury Madison & Sutro LLP

[57] ABSTRACT

An injection device includes a generally tubular outer body and a medicament cartridge assembly carried within the outer body. The cartridge assembly includes a glass container, a charge of medicament disposed within the glass container, iii) a plunger member rearwardly confining the medicament, and iv) a seal for sealing the forward portion of the glass container. A needle has a rearward end disposed proximate the seal, with the seal and needle being movable with respect to one another. A rigid needle cover member is normally maintained in an inoperative position and is movable relative to said body to a protective position wherein the needle cover member extends forwardly to cover the forward end of the needle. A releasable spring is releasable in response to a predetermined actuating procedure to drive a collet member forwardly within the outer body and thereby enable i) the cartridge assembly to move relative to the needle so that the rearward end of the needle pierces the seal to establish communication with the medicament, ii) the needle to move with respect to the body so that the needle projects outwardly from the forward end of the body, and iii) the needle cover to move relative to the body from the inoperative position to the protective position so that the needle cover member extends beyond the forward end of the needle.

6 Claims, 4 Drawing Sheets

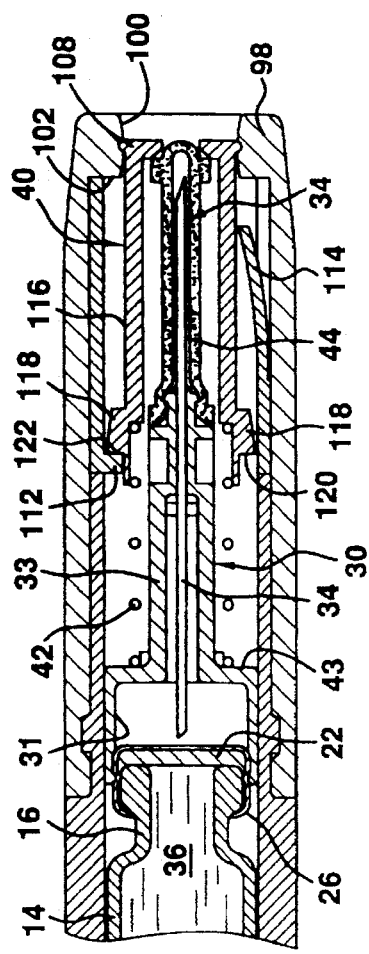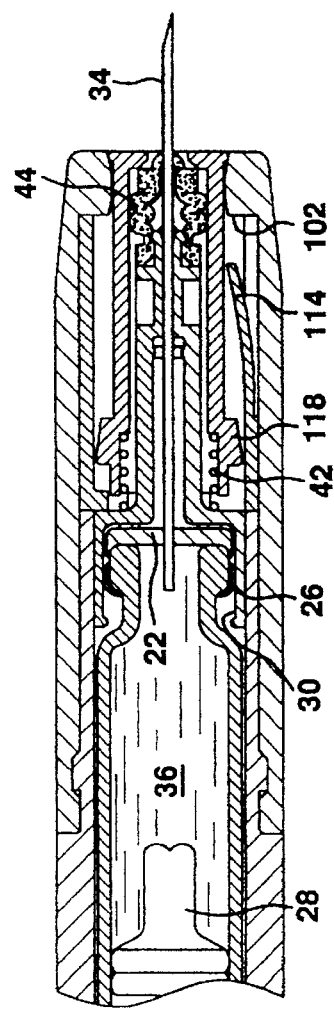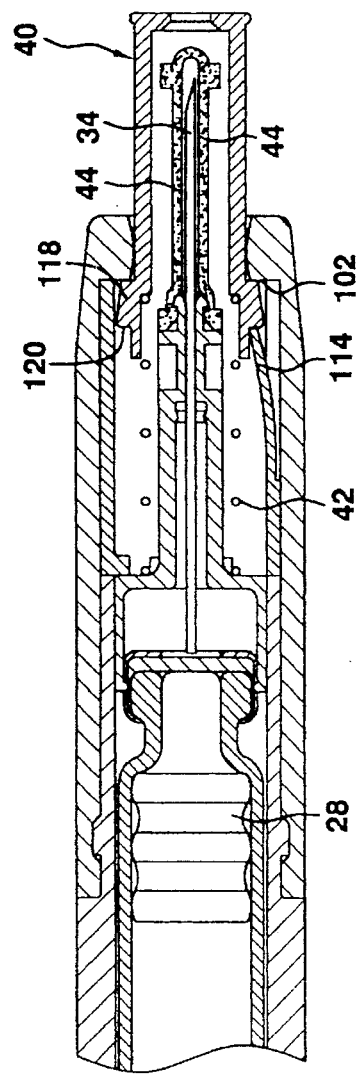

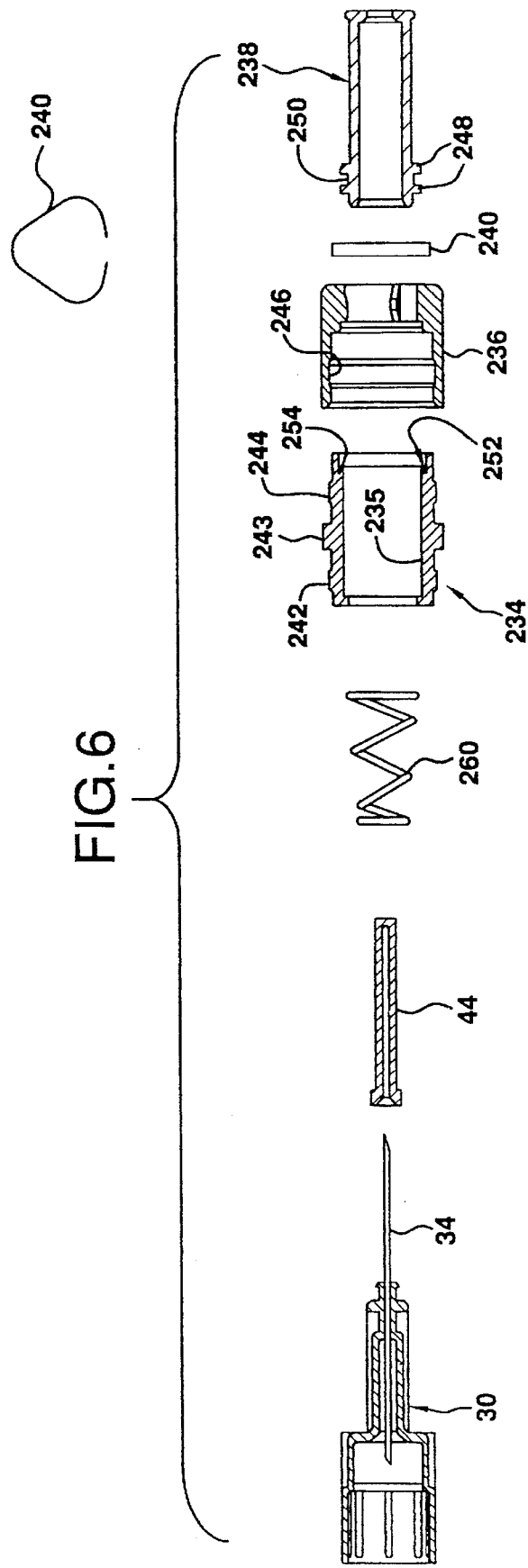

DENTAL CARTRIDGE ASSEMBLY AUTO-INJECTOR WITH PROTECTIVE NEEDLE COVER

Injection devices, such as automatic injectors, are well known and are described, for example, in U.S. Pat. Nos. 5,102,393 and 5,085,641, of common assignment herewith, and which are hereby incorporated by reference. Basically, an automatic injector is a device for enabling an individual to self-administer a dosage of a liquid medicament. An advantage of automatic injectors is that they contain a measured dosage of a liquid medicament in a sealed sterile condition capable of storage in such condition for extensive periods of non-use, during which period immediate injection of the stored dosage may be accomplished at any time. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's own tissue. Instead, an automatic injector includes a needle normally stored and concealed within a rigid outer housing. Also contained in the housing is a cartridge assembly, which comprises a sealed cartridge or container containing the dose of medicament, with a movable plunger rearwardly confining the medicament within the container. When a releasable spring assembly carried by the housing is released, the needle projects from a forward end of the housing, and the plunger is forced through the container to displace the medicament therefrom through the needle and into the flesh of the user.

In recently issued U.S. Pat. No. 5,295,965, of common assignment herewith, and hereby incorporated by reference, there is disclosed an automatic injector with the added feature that, after an injection operation, a protective rigid needle cover is spring biased against the skin and moves outwardly to cover the needle as it is withdrawn from the flesh. One advantage of such an arrangement is that the user does not see the needle even after the injection operation. Another advantage is that the protective cover prevents accidental or unwanted contact with the projecting needle after the injection operation. It should be appreciated that the needle-protective cover arrangement adds a level of complexity to the automatic injector, as it requires the automatic injector to effectuate relative movement of needle cover with respect to the main body. An even further level of complexity is added where the protective needle cover is initially retracted with respect to the injector body and has the capability of being locked in the extended position wherein it covers the projecting needle. Nevertheless, this type of injector has now sparked a significant amount of commercial interest.

In virtually all automatic injectors, the medicament container is made from a glass, metal, or plastic material. There is normally a significant expense associated with manufacturing such containers, and as a result, the total cost of manufacturing the injector is greater than what is desirable. Therefore, in an attempt to reduce some of the manufacturing costs, some injectors have employed what is known as a "dental cartridge" assembly, which incorporates a standard medicament dental cartridge or container that is manufactured in bulk quantities for the medical industry. The container employed in a dental cartridge assembly is tubular, preferably made of glass, and has a rearward portion with an inner diameter greater than the inner diameter of its forward portion. The rearward end of the container may be sealed by a medicament compatible plug inserted into the container. The forward end of the container is typically sealed by a medicament compatible rubber disk-shaped member that forms a circumferential seal with the forward lip of the tubular container by being clamped thereto by a retaining member. Dental cartridges or containers are used in various applications as shown, for example, by U.S. Pat. Nos. 3,413,974; 3,368,557; 3,678,931; 3,825,003; 4,445,895; 5,085,641; 5,226,895 and 5,226,896. Since such dental cartridges are mass produced, they are significantly less expensive than other types of cartridges, and it is thus desirable to incorporate them into automatic injectors. The incorporation of a dental cartridge in a cartridge assembly for an automatic injector is also advantageous in that it can easily be filled with medicament by standard automatic filling machines.

Those automatic injectors which utilize dental cartridges may be considered somewhat more difficult to engineer than those which employ containers that are specifically engineered to be used with the auto-injector. For example, in non-dental cartridge type automatic injectors, it is possible to assemble the hypodermic needle together with the cartridge so that the rearward end of the hypodermic needle is pre-mounted relative to the forward seal of the cartridge so that fluid communication between the needle and the medicament can be easily established during operation. For example, see the hereinbefore incorporated U.S. Pat. No. 5,295,965. This is to be contrasted with the dental cartridge type automatic injector, wherein the rearward end of the hypodermic needle is initially held spaced from the disk-shaped sealing member at the forward end of the container, and wherein relative movement between the hypodermic needle and the sealing member must take place in order for the rearward end of the needle to pierce the sealing member and thereby establish fluid communication between the hypodermic needle and the medicament. For example, in the hereinbefore incorporated U.S. Pat. No. 5,085,641, it is necessary for the forward sealing member of the dental cartridge assembly to be bulged forward by medicament pressure to be pierced by the rearward end of the needle.

In the automatic injector industry, there has been a need for an automatic injector that can provide the benefits of the protective needle cover assembly, while also having the cost-effectiveness obtained by use of a dental cartridge assembly. Heretofore, a device with such level of complexity has never been realized. It is thus an object of the present invention to satisfy the need expressed above in a most cost-effective and reliable manner. In accordance with this object, the present invention provides an automatic injection device pre-loaded with a charge of medicament for automatically self-administering the medicament upon actuation thereof. The injection device includes a generally tubular outer body, having a rearward end and a forward end, and a medicament cartridge assembly carried within the outer body. The cartridge assembly includes i) a glass container having a rearward portion thereof with a predetermined inner diameter and a forward portion thereof with an inner diameter smaller than the predetermined inner diameter, ii) a charge of medicament disposed within the glass container, iii) a plunger member rearwardly confining the medicament within the glass container and being slidably movable forwardly within the glass container, iv) a seal for sealing the forward portion of the glass container having the smaller inner diameter and for forwardly confining the medicament within the glass container. A needle is disposed forwardly of the cartridge assembly within the outer body. The needle has a forward end and a rearward end, with the rearward end being disposed proximate the seal and being separated from the medicament by the seal when the injection device is in a storage condition. The seal and the needle are movable with respect to one another so that the rearward end of the needle pierces the seal to establish communication with said medicament during an injection operation. The needle and said body being movable with respect to one another so that the needle projects outwardly from the forward end of the body during the injection operation. A rigid needle cover member is normally maintained in an inoperative position wherein the forward end of the needle is permitted to extend forwardly beyond the needle cover member and is movable relative to the body to a protective position wherein the needle cover member extends forwardly beyond the forward end of the needle. The needle cover is movable from the inoperative position to the protective position as a result of the injection operation. A locking arrangement locks the needle cover in the protective position after the injection operation so as to maintain the cover member extending forwardly beyond the forward end of the needle. A releasable drive assembly comprises a releasable spring and a collet member. The releasable spring is releasable in response to a predetermined actuating procedure to drive the collet member forwardly within the outer body and thereby enable i) the cartridge assembly to move relative to the needle so that the rearward end of the needle pierces the seal to establish communication with the medicament, ii) the needle to move with respect to the body so that the needle projects outwardly from the forward end of the body, and iii) the needle cover to move relative to the body from the inoperative position to the protective position so that the needle cover member extends beyond the forward end of the needle.

BRIEF DESCRIPTION OF THE DRAWINGS

FIG. 2 is an enlarged longitudinal sectional view of the forward portion of the automatic injection device shown in FIG. 1;

FIG. 3 is a longitudinal sectional view similar to FIG. 2, but showing the automatic injection device after it has been actuated;

FIG. 4 is a longitudinal sectional view similar to that of FIG. 3, but showing the injection device of the first embodiment in a needle protective position, wherein the needle cover member is extended in protective relation over a projecting needle;

FIG. 6 is an exploded view of various components utilized in effectuating operation of the needle cover assembly in accordance with the second embodiment of the present invention.

FIG. 7 is a plan view of a retaining spring utilized in the needle cover assembly in accordance with the second embodiment of the present invention.

DETAILED DESCRIPTION OF THE DRAWINGS

Figure 1:
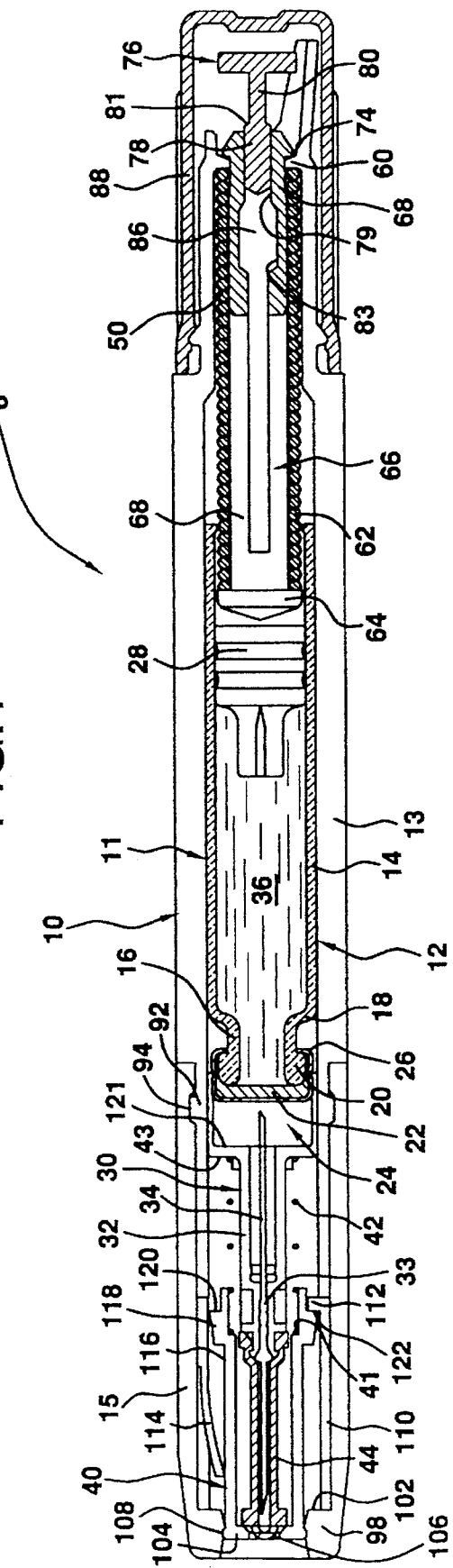
FIG. 1 is a longitudinal sectional view of a first embodiment in accordance with the principles of the present invention.

Referring now, more particularly to the drawings, there is shown in FIG. 1 an automatic injector, generally indicated at 8, which embodies the principles of the present invention. The automatic injector has an outer housing or body, generally indicated at 10, and a dental cartridge assembly 11 contained within the body. The outer body comprises a main elongated tubular housing member 13, and a forwardly disposed elongated tubular housing member 15.

The dental cartridge assembly 11 comprises a dental cartridge or container 12, which is tubular in form, and usually made of glass, although it can also be made of plastic or metal. The tubular container 12 is opened at its opposite ends, and is necked-down at its forward end. More particularly, a major portion 14 of the container 12 extends rearwardly of the forward necked down forward portion 16 and has a predetermined inner diameter which is larger than the inner diameter of the necked down forward portion. These portions can be more clearly discerned in FIG. 2. The container has an inwardly extending peripheral shoulder 18, which integrally connects the main rearward portion of the container with the smaller diameter forward portion of the container. The forwardmost end (generally indicated at 24) of the container has a radially outwardly extending flange 20 which receives a seal member 22 to close off the forward end. The seal member 22 is peripherally secured to the annular forwardmost surface or lip of flange 20 at the forward end of the container 12 by means of an annular metallic clamping ring 26. A plunger 28 closes the open rearward end of the container 12 and is mounted therein for forward sliding movement in sealing relation with the interior surface thereof. Preferably, the plunger 28 is a "nipple-type" plunger for substantially expelling all medicament from the container 12. In another preferred arrangement, the plunger 28 may be somewhat stunted, and a "top-hat" configuration can be used for the seal member in order to substantially expel all medicament from container 12. The aforementioned arrangements for the nipple and/or seal member are disclosed in the parent patent application Ser. No. 08/280,884, which is hereby incorporated by reference. It should be appreciated, however, that the aforementioned plunger and/or arrangements are merely preferred and that the present invention contemplates that any known type of plunger or sealing arrangement can be used.

A slidable needle hub assembly, generally indicated at 30, has a cup-shaped rearward portion 31 opened towards the rear of the body 10. The forward end of the container 12, including clamp ring 26, extends partially into the rearward portion 31 in telescopic relation. An exterior periphery of the forward end of cartridge assembly 11, i.e., the radially outermost surface of clamp ring 26, frictionally engages the rearward portion of the cylindrical inner surface of the rearward portion 31. The needle hub assembly 30 has a substantially narrowed diameter forward portion 32 thereof disposed in surrounding relation to a hypodermic needle 34. The needle 34 is secured at a central peripheral portion 33 thereof to the hub assembly 30.

The forward portion of the needle 34 may be covered by a protective sheath 44 to maintain the sterility of the needle and to act as a shock absorber for the cartridge assembly 11 as the cartridge assembly is moved forwardly towards the front end of the body during an injection procedure. A similar sheath is disclosed in U.S. Pat. No. 3,882,863, hereby incorporated by reference.

A tubular protective needle cover member 40 is disposed in surrounding relation to the forward portion of the needle. The needle cover member is substantially tubular, and has a rearward portion of slightly greater inner diameter so as to present a rearwardly facing annular surface 41. A coil spring 42 has its forward volute resting upon annular surface 41 and its rearward volute resting upon a forwardly facing annular surface 43 of the rearward cup-shaped portion 31 of needle hub assembly 30 so as to be slightly compressed therebetween before an injection operation. The cover member is spring biased by the coil spring 42 to move forwardly in protective relation over the needle after an injection operation wherein the needle projects from the forward end of the device. The needle cover member will be described in greater detail, infra.

A releasable drive assembly 50 is provided within the rearward portion of the main housing member 13. The drive assembly 50 includes a coil spring 62, and a collet member generally indicated at 66. The main housing member 13 is formed with an interior annular flange 60 spaced slightly inwardly from the rearward end thereof. The forward surface of the annular flange 60 is adapted to be engaged by a rearward volute of the coil spring 62, which operates as a releasable energy source for the injector of the present invention. It is understood that the present invention is not limited to the use of a coil spring and that any releasable energy source, such as an air spring, or chemical expansion reaction, may be used. The forward volute of the coil spring 62 engages a rearwardly facing surface of a forward flange 64 of the collet member 66.

The collet member 66 extends rearwardly from the forward flange 64 thereof within the coil spring 62. The rearward end portion of the collet member 66 is split so as to form a plurality (two) of rearwardly extending spring fingers 68. The rearward peripheral portion of the fingers 68 are formed with radially outwardly extending flanges presenting forwarding facing locking surfaces 74 which are adapted to engage along a generally radially extending plane with the rearwardly facing surface of the interior annular flange 60 of the housing member 13.

As shown in FIG. 1, a safety actuating pin member, generally indicated at 76, is disposed in cooperating relation with the resilient fingers 68 in a storage position and includes a forward portion 78 which extends inwardly between the resilient fingers 68. The safety actuating member 76 also includes an intermediate portion 80 of a reduced diameter with respect to the forward portion 78, there being a frustoconical transition 81 between the two portions. The larger forward portion 78 extending between fingers 68 is cylindrical in form and, in the position shown in FIG. 1, engages the rearward generally arcuate inner facing surfaces 79 of the spring fingers 68 so as to prevent the fingers from moving radially inwardly toward one another, thereby maintaining the locking surfaces 74 of the spring fingers 68 in engagement with the rearwardly facing locking surfaces of flange 60. Thus, coil spring 62 is retained in a stressed condition between the forward flange 64 of the collet member 66 and the forwardly facing surface of the interior flange 60 of housing member 13. As shown in FIG. 1, immediately forwardly of the rearward arcuate inner facing surfaces 79, the spring fingers 68 have arcuate inner surfaces 83 of a greater diameter than surfaces 79 so as to define a relatively large diameter space 86 in comparison to the space defined by surfaces 79. As also shown in FIG. 1, a cap structure 88 is in a storage position, and covers actuating member 76.

The rearward end of the tubular housing member 15 is telescopingly received over the forward portion of the main tubular housing member 13. More particularly, the housing member 13 has an annular flange 92 radially extending outwardly from an exterior surface thereof. The housing member 15 has an annular groove 94 formed in the interior surface thereof toward the rearward portion thereof. The forward housing member 15 is secured to the main housing member 13 by rearwardly sliding the rearward end of the housing member in telescoping relation over the forward end of the housing member 13 until the annular flange 92 of the housing member 13 snaps into the annular groove 94 of the housing member 15. The forwardmost portion of the housing member 15 has a radially inwardly extending flange 98. The flange 98 has a generally inwardly bulging axially extending interior surface 100, and a generally flat annular rearwardly facing surface 102, as shown.

The forward end of the tubular protective needle cover member 40 has a radially inwardly extending flange 104, having a central aperture 106. The forward end of the tubular needle cover also has a small annular ridge 108 radially extending outwardly from the forwardmost portion of the cylindrical exterior surface thereof. When the automatic injector is in its storage condition, i.e., prior to use, the needle cover is retained within the forward housing member 15 by virtue of a frictional, interference fit between the ridge 108 and the inwardly bulging interior surface 100 of flange 98. In an alternative configuration, the surface 100 of flange 98 may be provided with a slight annular notch adapted to receive the annular ridge 108 of the needle cover 40 to retain the needle cover within the forwardly disposed housing member 15 against the bias of spring 42 prior to an injection operation.

A somewhat tubular leaf spring element 110 is disposed within the housing member 15 between the rearwardly facing surface 102 flange 98 and the forwardmost end of the main housing member 13. More specifically, the spring element is cylindrical, except for the provision of a radially inwardly extending arcuate projection 112 disposed at the rearwardmost end thereof, and a spring tab member 114 cut into the forward portion of the spring element. The spring tab member 114 is elongated, flexible, and integrally connected at its rearward end with the spring element 110 generally at a longitudinal midpoint of the spring element. The tab member 114 extends forwardly and inwardly from its rearward end toward its forward end and has its forward end disposed in resilient, spring biased engagement with an exterior cylindrical surface 116 of the needle cover 40.

The needle cover 40 has an annular flange 118 extending radially outwardly from the exterior surface 116 thereof and disposed slightly spaced from the rearward end thereof. The flange 118 has a rearwardly facing annular surface 120, which engages a forwardly facing surface 122 of the inwardly extending projection 112 when the needle cover is disposed within the forward housing member 15 in its inoperative position as shown in FIGS. 1 and 2. This engagement prevents the needle cover 40 from being pushed back into the body 12 to a greater extent than what is desirable. When the needle cover 40 is deployed during an injection operation, the spring tab member 114 is caused to ride over and snap behind the flange 118. The forward end of the spring tab member 114 then rests behind or upon surface 120 of the flange 118 and thereby prevents rearward movement of the needle cover 40. Thus, the spring member 114 and flange 118 operate as a locking arrangement for locking the needle cover 40 in its protective position after an injection operation.

To effectuate an injection, the cap structure 88 is removed, and the user grasps body 10 in one hand and places the forward end of the injector against the portion of flesh to be injected. Next, the safety actuating pin member 76 is moved forwardly by a thumb or other finger so that the forward larger portion 78 of the actuating member 76 is moved into the larger space 86 defined by inner arcuate surfaces 83 of spring fingers 68. During such movement, the narrowed diameter intermediate portion is also moved into the fingers and permits the rearward portion of the fingers to flex inwardly to an extent sufficient such that the locking surfaces 74 are moved off of the flange 60, allowing the collet member 66 to move forwardly under the action of the spring 62. The collet 66 continues to move forwardly, while the safety actuating pin member 76 is left behind in captured relation by the rearward flange 60 of housing member 13.

The collet member 66 during its forward movement is forced against the rearward surface of plunger 28. This in turn causes the entire cartridge assembly 11 to move forwardly within the body 10 so that the forward end of the needle 34 projects from the forward end of the injector while compressing sheath 44 and spring 42. This is clearly shown in FIG. 3. Further movement of the cartridge assembly 11, as also shown in FIG. 3, causes the forwardly facing surface 43 of hub assembly 30 to engage the rearwardmost end of needle cover member 40 so as to move the needle cover member 40 forwardly so that the ridge 108 thereof is forced out of interference engagement with the radially inwardly bulging surface 100 of housing member 15. This slight movement of the needle cover member 40 will enable the cover member to be moved fully outwardly into protective relation over the needle 34 when the needle is withdrawn from the flesh. As can also be appreciated from FIG. 3, the forwardly facing surface 43 of the hub assembly 30 eventually engages the rearward facing surface of projection 112, which halts any further movement of the hub assembly 30. Continued force provided and momentum by the coil spring 62, however, causes the forward portion of the exterior periphery of cartridge assembly 11, i.e., the radially outermost surface of clamp ring 26, to slide forwardly in frictional engagement with the rearward portion of the cylindrical inner surface of the portion 31 of hub assembly 30. As a result, the rearward end of the needle 34 pierces the seal member 22 to establish communication with the medicament 36 through the seal.

After the forwardmost portion of the cartridge assembly extends as far as possible into the rearward portion 31 of the hub assembly 30 so as to engage the rearwardly facing annular surface 121 thereof, the continued spring-biased force of the collet member 66 acts to move the plunger 28 forwardly through the container 12. This movement of the plunger 28 pressurizes the liquid medicament 36 and begins to force it through the needle 34.

As shown in FIG. 4, which shows the automatic injector after the needle is withdraw from the flesh of an individual, the needle cover member 40 is permitted to move forwardly with respect to the body 10 from its inoperative position (as shown in FIGS. 2 and 3) to a protective position wherein it extends beyond the forward end of the needle 34 with the needle projecting outwardly from the forward end of the body. The needle cover member 40 will continue to move forward until the forward facing surface of flange 118 engages the rearwardly facing surface 102 of housing member 15. When the needle cover reaches its forwardmost position, the spring tab member 114 rides over and snaps behind flange 118 to lock the needle cover is its protective position covering the needle 34. In addition, when the needle cover moves to its protective position, the resilient sheath 44 is permitted to relax and move outwardly to cover the needle 34 within the cover 40 to further insulate the now blood contaminated needle.

Figure 5:
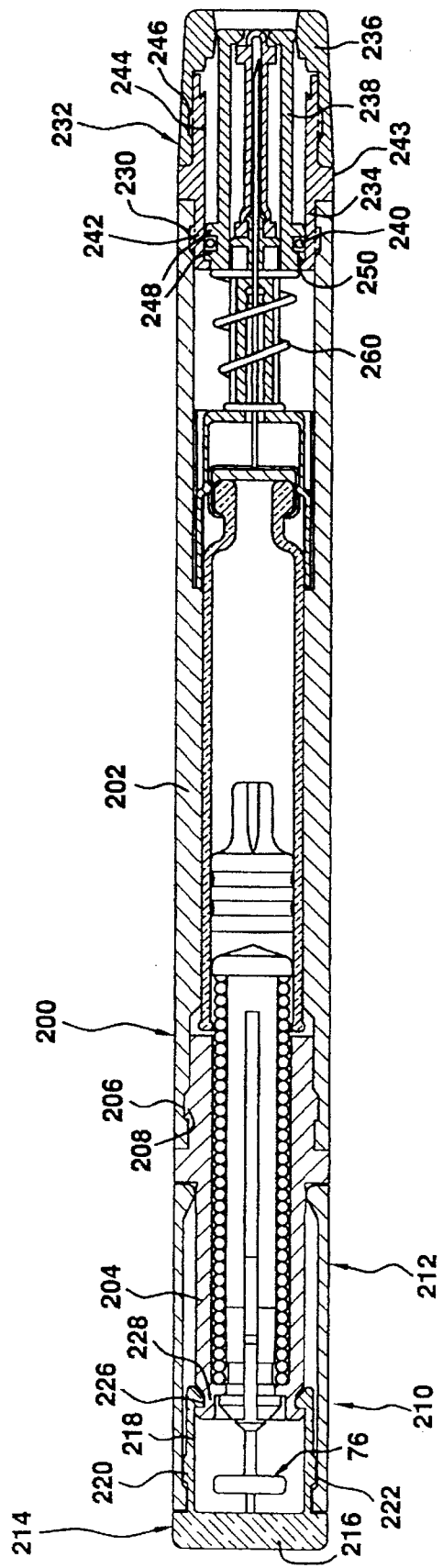
FIG. 5 is a longitudinal sectional view of a second embodiment of the automatic injection device is accordance with the principles of the present invention.

FIG. 5 shows another embodiment in accordance with the principles of the present invention. The embodiment shown in FIG. 5 is substantially identical to the embodiment shown in FIG. 1, with the exception of the differences about to be described. Common elements between the two embodiments are designated by the same reference numerals.

Beginning with the rearward portion of the injection device, it can be appreciated that the outer housing or body 200 is formed from two separate housing members, including a forward housing member 202 and a rearward housing member 204. The rearward interior surface of the forward housing 202 is provided with an annular groove 206. The rearward housing member 204 has an annular flange 208 extending radially outwardly from the exterior surface thereof and is slightly spaced from the forwardmost end of the housing member 204. The flange 208 is received within the groove 206 to thereby secure the rearward housing member 204 to the forward housing member 202.

A safety cap member 210 is provided and is also formed from two separate structures, including a tubular forward structure 212 and a rearward plug 214 that is inserted into the rearward end of the tubular structure 212. The plug 214 has a circular end portion 216 and a cylindrical wall portion 218 extending forwardly therefrom into the interior confines of the tubular structure 212. The cylindrical wall portion 218 has an exterior annular flange 220, which is received in an internal annular groove 222 provided in the rearward portion of the forward tubular structure 212 so as to secure the plug 214 to the forward structure 212. The cylindrical wall 218 has an inwardly extending annular flange 226 at the forward end thereof. An annular groove 228 is disposed within the exterior surface of the rearward housing member 204. The flange 226 of the plug member 214 is received within the groove 228 to enable the cap member 210 to be removably secured to the rearward housing member 204. The cap member 210 can be removed from the rearward housing member 204 by grasping the exterior surface of the forward housing member 202 with the palm and fingers of one hand and pulling the cap member 210 rearwardly with the other hand so that the annular flange 226 rides out of the annular groove 228. Further features and advantages of the interrelation between the cap member 210 and the rearward housing member 204 can be appreciated from U.S. Pat. No. 5,085,641, which is hereby incorporated by reference. For example, preferably, the cap structure 210 is constructed and arranged such that its clip must be rotatably aligned with an indicia on the rearward housing member before it can be removed, as disclosed in the aforementioned patent. Removal of the cap member 210 permits manual access to the safety pin 76 as with the first embodiment.

At the forward end of the forward housing member 202 is an annular interior groove 230. A forward end cap assembly, generally indicated at 232, is secured to the forward end of the tubular housing member 202. More specifically, as will be described in conjunction with FIGS. 5-7, the end cap assembly 232 comprises a tubular needle housing member 234, a tubular end cap member 236 secured to the needle housing member 234, a generally tubular needle cover member 238 disposed within the needle housing member 234, and a substantially triangular (see FIG. 7), radially outwardly biased retaining spring 240 for locking the needle cover member 238 in the extended, protective position. The needle housing member 234 has a forwardly disposed exterior annular flange 242, which is received within the internal annular groove 230 of the forward housing member 202, so as to secure the end cap assembly 232 to the forward housing member 202. The needle housing member 234 also includes a centrally disposed exterior annular flange 243 of a greater diameter than flange 242. The flange 243 engages the forward annular surface of the housing member 202 to prevent the housing member from extending therebeyond. Forwardly spaced from flange 243 is a third flange 244 radially extending from the exterior surface of housing member 234. The flange 244 is received within an annular groove 246 disposed within the interior surface of the end cap member 236 so as to secure the needle housing member 234 to the end cap member 236. The forward portion of the needle housing member 234 has an annular groove 252 forming part of the interior surface thereof. The groove 252 has a rearward and radially outwardly extending surface 254, forming somewhat of a "V"-shaped notch, as shown.

The needle cover member 238 has a pair of longitudinally spaced annular flanges 248 extending radially outwardly from an exterior surface thereof. The flanges 248 define a groove 250 therebetween, within which retaining spring 240 is retained. Upon activation of the injection device of the second embodiment, the needle cover member 238 is moved outwardly to the protective position in substantially the same manner described with respect to the first embodiment.

The retaining spring 240 is biased for radially outward expansion against the interior cylindrical surface 235 of the needle housing member 234. During movement of the needle cover member 238 forwardly under the force of a conical coil spring 260 into the protective position, the retaining spring 240 is moved in sliding engagement with the interior cylindrical surface 235 of the needle housing member 234. When the retaining spring 240 reaches the groove 252, it is able to expand radially outwardly into said groove.

The expansion of the retaining spring 240 into the groove 252 provides for an interference between the needle cover member 238 and the needle housing member 234 so as to lock the needle cover member 238 in the forwardly extending, protective position. More particularly, any attempt to move the needle cover member 238 back into the injector housing will be prevented, as the surface 254 of the groove 252 formed in needle housing member 234 will engage spaced portions of the rearwardly facing surface of the retaining spring 240, which spring continues to be retained between flanges 242 of cover member 238. As a result, the needle cover member 238 is prevented from moving rearwardly into the auto-injector.

It thus will be seen that the objects of this invention have been fully and effectively accomplished. It will be realized, however, that the foregoing preferred specific embodiment has been shown and described for the purpose of this invention and it is subject to change without departure from such principles. Therefore, this invention includes all modifications encompassed within the spirit and scope of the following claims.

What is claimed is:

1. An automatic injection device pre-loaded with a charge of medicament for automatically self-administering said medicament upon actuation thereof, comprising:

a generally tubular outer body having a rearward end and a forward end;

a medicament cartridge assembly carried within said outer body, said cartridge assembly including i) a glass container having a rearward portion thereof with a predetermined inner diameter and a forward portion thereof with an inner diameter smaller than said predetermined inner diameter, ii) a charge of medicament disposed within said glass container, iii) a plunger member rearwardly confining said medicament within said glass container and being slidably movable forwardly within said glass container, iv) a seal for sealing the forward portion of said glass container having said smaller inner diameter and for forwardly confining said medicament within said glass container, a needle disposed forwardly of said cartridge within said outer body, said needle having a forward end and a rearward end, said rearward end of said needle being disposed proximate said seal and being separated from said medicament by said seal when said injection device is in a storage condition, at least one of said seal and said needle being movable with respect to the other so that said rearward end of the needle pierces said seal to establish communication with said medicament during an injection operation, and said needle being movable with respect to said body so that said needle projects outwardly from the forward end of said body during said injection operation, a rigid needle cover member normally maintained in an inoperative position wherein the needle cover is retracted with respect to said body so that the forward end of said needle is permitted to extend forwardly beyond said needle cover member and being movable relative to said body to a protective position wherein the needle cover member extends forwardly beyond the forward end of said needle with the needle projecting outwardly from the forward end of said body, said needle cover being movable from said inoperative position to said protective position as a result of said injection operation;

a locking arrangement for locking said needle cover in said protective position after said injection operation so as to maintain said cover member in said protective position extending forwardly beyond the forward end of said needle; and a releasable drive assembly comprising a releasable spring and a collet member, said releasable spring being releasable in response to a predetermined actuating procedure to drive said collet member forwardly within said outer body and thereby enable i) at least one of said seal and said needle to move with respect to the other so that said rearward end of said needle pierces said seal to establish communication with said medicament, ii) the needle to move with respect to the body so that the needle projects outwardly from the forward end of the body, and iii) the needle cover to move relative to said body from the inoperative position to the protective position so that the needle cover member extends beyond the forward end of the needle with the needle projecting outwardly from the forward end of the body.

2. An automatic injection device according to claim 1, wherein said needle cover member is normally contained within said tubular outer body when in said inoperative position, said needle cover member having a portion of an exterior surface thereof disposed in locking engagement with an interior surface of said tubular outer body so as to retain said needle cover within said outer body prior to said injection operation.

3. An automatic injection device according to claim 2, further comprising a cover projection spring disposed between said needle cover and said cartridge assembly, said projection spring being increasingly compressed upon release of said releasable drive assembly and movement of said cartridge assembly forwardly within said outer body until potential energy building in said projection spring as a result of said compression is sufficient to cause the needle cover to move out of locking engagement with the interior surface of the outer body, at which time the potential energy of said projection spring is released to move said needle cover outwardly from said outer body toward said protective position.

4. An automatic injection device according to claim 3, wherein said locking arrangement comprises a biasing member disposed between said cover member and said inner surface of said outer body, said biasing member being normally inoperative to permit said needle cover member to move outwardly from said outer body into said protective position during said injection operation, and said spring being moved to an operative position wherein it provides a locking interengagement between said cover member and said inner surface of said outer body.

5. An automatic injection device according to claim 4, wherein said locking arrangement further comprises an annular ridge formed on an exterior surface of said cover member, said annular ridge having a rearwardly facing annular surface, said biasing member comprising a leaf spring element which slidingly engages an exterior surface of said cover member forwardly of said ridge during movement of said cover member from said inoperative position to said protective position, said leaf spring element constructed and arranged to ride over said ridge to rigidly engage the rearwardly facing annular surface of said ridge to thereby prevent rearward movement of said cover member after it reaches said protective position.

6. An automatic injection device according to claim 1, wherein at least one of said needle and said glass container moves relative to the upon release of said releasable drive assembly so that the rearward end of said needle enters the forward portion of said glass container and thereby pierces said seal to establish communication with said medicament.

* * * * *